US011709160B2

(12) United States Patent
Hickerson et al.

(10) Patent No.: US 11,709,160 B2
(45) Date of Patent: Jul. 25, 2023

(54) SKIN SAMPLE CULTURE APPARATUS

(71) Applicant: The University of Dundee, Dundee (GB)

(72) Inventors: Robyn Patricia Hickerson, Balmullo (GB); Michael John Conneely, Dundee (GB)

(73) Assignee: The University of Dundee, Dundee (GB)

( * ) Notice: Subject to any disclaimer, the term of this patent is extended or adjusted under 35 U.S.C. 154(b) by 1009 days.

(21) Appl. No.: 16/302,787

(22) PCT Filed: May 22, 2017

(86) PCT No.: PCT/GB2017/000080
§ 371 (c)(1),
(2) Date: Nov. 19, 2018

(87) PCT Pub. No.: WO2017/198988
PCT Pub. Date: Nov. 23, 2017

(65) Prior Publication Data
US 2019/0300830 A1 Oct. 3, 2019

(30) Foreign Application Priority Data

May 20, 2016 (GB) ..................................... 1608899

(51) Int. Cl.
*C12M 1/00* (2006.01)
*C12M 3/00* (2006.01)
(Continued)

(52) U.S. Cl.
CPC ....... *G01N 33/5005* (2013.01); *A01N 1/0242* (2013.01); *A01N 1/0263* (2013.01);
(Continued)

(58) Field of Classification Search
CPC .. A01N 1/0242; A01N 1/0263; A01N 1/0278; C12M 21/08; C12M 23/38;
(Continued)

(56) References Cited

U.S. PATENT DOCUMENTS

| 5,914,264 A | 6/1999 | Korman |
| 6,057,150 A | 5/2000 | Lee et al. |

(Continued)

FOREIGN PATENT DOCUMENTS

| CN | 201535769 U | 7/2010 |
| KR | 1020160012663 A | 2/2016 |
| WO | 0193771 A1 | 12/2001 |

OTHER PUBLICATIONS

Chin et al., In Vivo Accelertion of Skin Growth Using a Servo-Controlled Stretching Device, Tissue Engineering: Part C, vol. 16, No. 3, 2010, pp. 397-405.
(Continued)

*Primary Examiner* — Lydia Edwards
(74) *Attorney, Agent, or Firm* — RatnerPrestia

(57) ABSTRACT

A skin sample culture apparatus which has a base frame, with a skin sample receiving surface upon which at least part of the skin sample may be placed and which extends across an area defined by the shape of the frame. A securing member which is releasably connectable to the base frame and a grip which holds the skin sample under tension. The apparatus may include a tensioner to hold the sample under tension and means for introducing a fluid to the upper or lower surface of the sample.

13 Claims, 12 Drawing Sheets

(51) Int. Cl.
  *C12M 1/12* (2006.01)
  *C12M 1/42* (2006.01)
  *G01N 33/50* (2006.01)
  *C12N 5/071* (2010.01)
  *A01N 1/02* (2006.01)
  *C12Q 1/6876* (2018.01)
  *G01N 1/36* (2006.01)

(52) U.S. Cl.
  CPC .......... *A01N 1/0278* (2013.01); *C12M 21/08* (2013.01); *C12M 23/38* (2013.01); *C12M 23/46* (2013.01); *C12M 23/48* (2013.01); *C12M 35/04* (2013.01); *C12N 5/0629* (2013.01); *C12Q 1/6876* (2013.01); *G01N 1/36* (2013.01)

(58) Field of Classification Search
  CPC ...... C12M 23/46; C12M 23/48; C12M 35/04; C12N 5/0629; C12Q 1/6876; G01N 1/36; G01N 33/5005
  See application file for complete search history.

(56) References Cited

U.S. PATENT DOCUMENTS

| | | |
|---|---|---|
| 2003/0034267 A1 | 2/2003 | De Luca et al. |
| 2010/0323438 A1* | 12/2010 | Porter .................... C12M 35/04 435/293.1 |
| 2011/0159582 A1 | 6/2011 | Israelowitz et al. |
| 2011/0172683 A1 | 7/2011 | Yoo et al. |
| 2015/0018948 A1 | 1/2015 | Shirwaiker et al. |

OTHER PUBLICATIONS

Hutchinson et al., Novel Skin Stretching Device, May 2012, 138 pages.
International Search Report issued in PCT/GB2017/000080, dated Nov. 11, 2017, 7 pages.
Written Opinion of the International Searching Authority issued in PCT/GB2017/000080, dated Nov. 17, 2017, 10 pages.
GB Search Report issued in Application No. GB 1608899.9, dated Nov. 16, 2016, 2 pages.

* cited by examiner

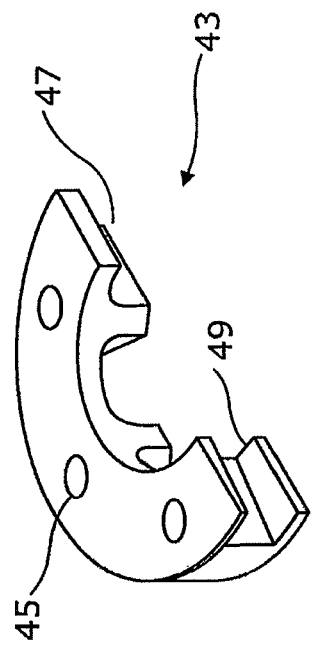
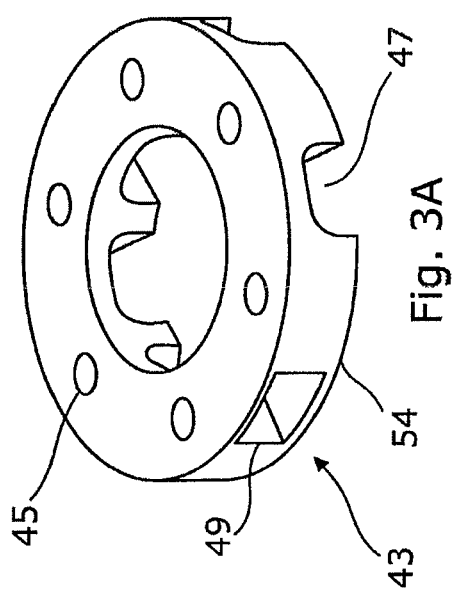
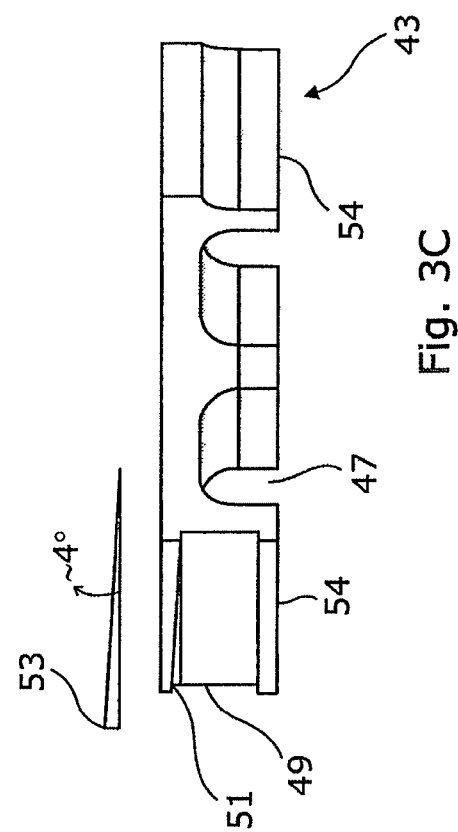

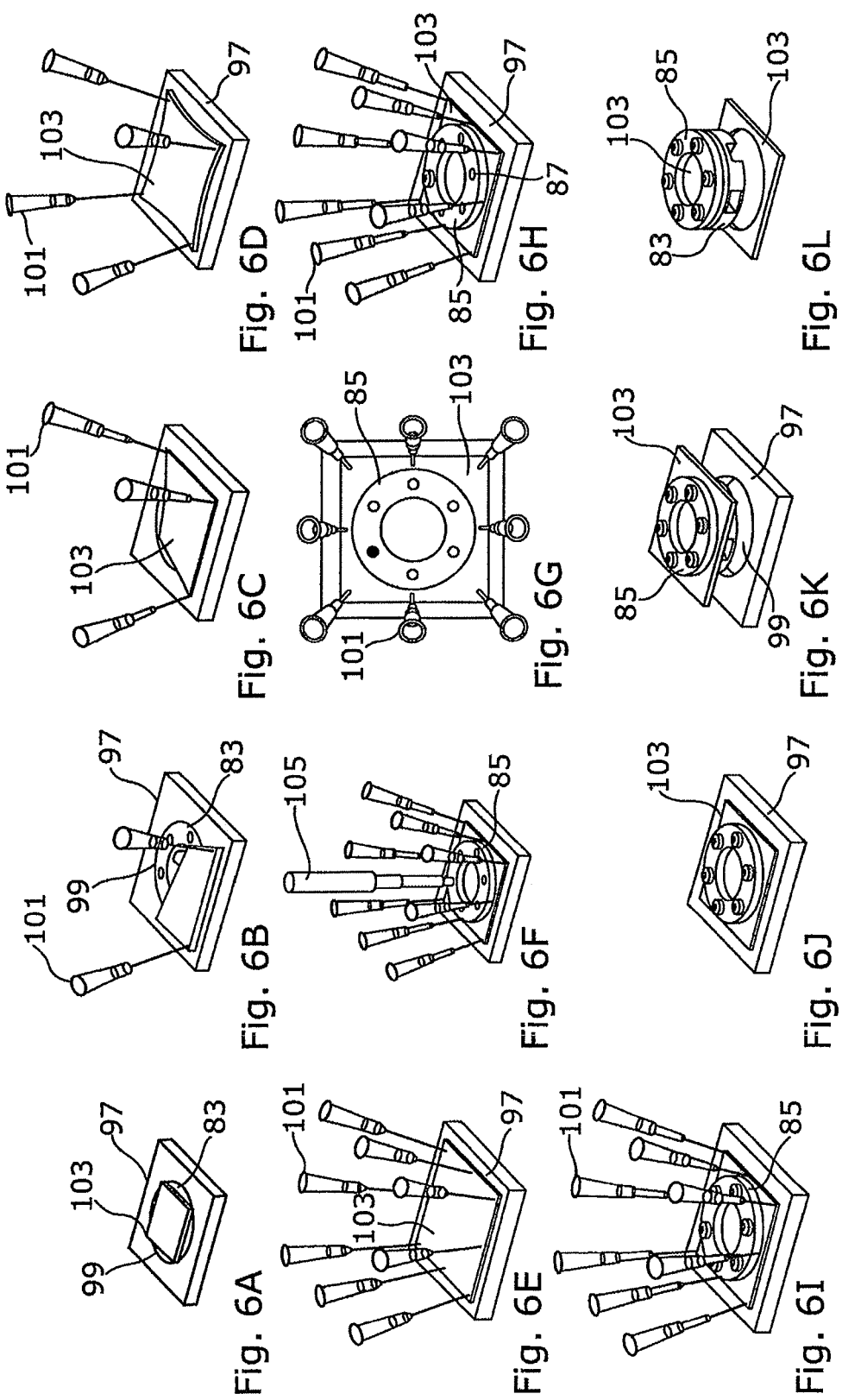

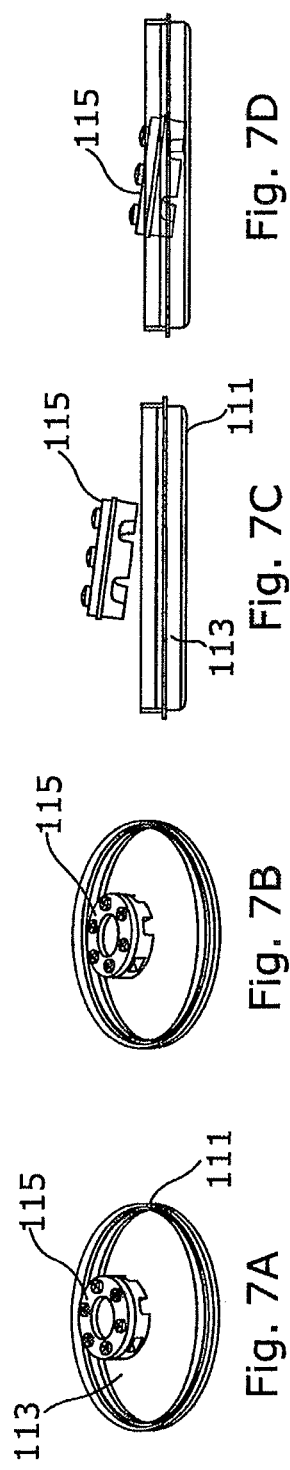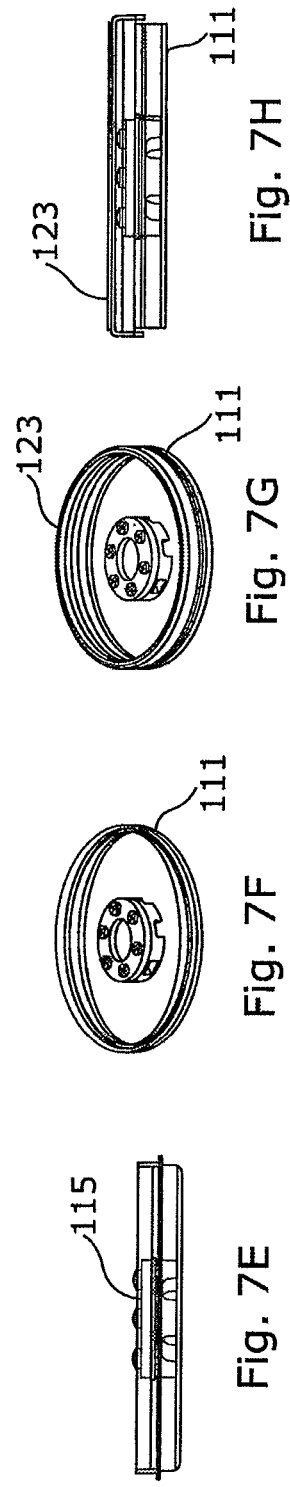

SKIN SAMPLE CULTURE APPARATUS

CROSS-REFERENCE TO RELATED APPLICATIONS

This application is the U.S. National Phase Application of PCT/GB2017/000080, filed May 22, 2017, which claims priority to Great Britain Application No. GB1608899.9, filed May 20, 2016, the contents of such application being incorporated by reference herein.

INTRODUCTION

The present invention relates to a skin sample culture apparatus and in particular to a skin sample storage apparatus which uses a culture medium to maintain the viability of the skin sample.

BACKGROUND TO THE INVENTION

Skin is the strong outer covering of vertebrate animals. Other animal coverings such as the arthropod exoskeleton have a different developmental origin, structure and chemical composition.

In mammals, the skin is an organ made up of multiple layers of ectodermal tissue covering the underlying tissue, ligaments, bones and internal organs. It acts as a sensory organ, protects the body against pathogens, ultraviolet damage, excessive water loss, provides insulation, temperature regulation and produces vitamin D.

The thickness of skin varies from location to location on an organism. In humans for example the skin located under the eyes and around the eyelids is the thinnest skin in the body at 0.5 mm thick whereas the skin on the palms and the soles of the feet is 4 mm thick and is around 1.4 mm thick on the back.

Mammalian skin is composed of two primary layers, the epidermis and the dermis. The epidermis is a stratified, cornified epithelium with specific barrier functions which is supported by the complex extracellular matrix environment of the dermis. In order for skin to retain its normal appearance and to function fully in a normal manner, both layers of the skin need to be present.

The epidermis forms a protective barrier over the body's surface, is responsible for keeping water in the body, protecting from UV light and preventing pathogens from entering.

The epidermis contains no blood vessels and cells in the deepest layers are nourished by diffusion from blood capillaries extending to the upper layers of the dermis.

The dermis comprises connective tissue and cushions the body from stress and strain. The dermis provides tensile strength and elasticity to the skin through an extracellular matrix composed of collagen fibrils, microfibrils, and elastic fibers. The dermis is tightly connected to the epidermis through a basement membrane and is structurally divided into two areas: a superficial area adjacent to the epidermis, called the papillary region, and a deep thicker area known as the reticular region.

Samples of skin may be removed from an animal body for the purpose of analysis or in order to grow a sample of skin where a skin graft is required.

Skin grafting is an essential component of reconstructive surgery after burns, trauma, tumor excision, and correction of congenital anomalies. The best possible skin available for grafting is skin from the same patient taken from a donor site elsewhere on the body which is referred to as an autograft. Suitable skin graft donor sites are limited by body surface area and may also be affected by previous graft harvest or trauma. In patients suffering from large burns with limited donor skin sites, cadaver allografts are commonly used for temporary skin coverage.

In all cases, there is a need to maintain the skin sample in a healthy state and to slow or completely arrest deterioration of the quality of the sample whilst it is being stored.

Reliable skin models which recapitulate the features of live skin are essential for the investigation of cutaneous biology and drug discovery. Full-thickness ex vivo skin culture systems have been used extensively. The global market for ex vivo skin models includes the academic researcher, the pharmaceutical industry and the cosmetic industry with regards to safety and efficacy assessment for the increasing number of products developed for topical application. Furthermore, the development of such a model system is of an increasing priority due to the European Community regulation that bans the use of animal testing for cosmetic ingredients.

A number of prior art documents were found. The most relevant documents were related to but none disclosed a device as per the present disclosure. The most relevant documents were U.S. Pat. No. 5,914,264 and CN 201535769. U.S. Pat. No. 5,914,264 discloses a method of growing vertebrate skin in vitro. Part of the process involves creating a method for stretching the skin so as to enhance skin growth by positioning the skin segment in an artificial cell-growth medium and subjecting the skin segment to stretching forces while the skin segment is in the medium.

CN 201535769 describes an apparatus for measuring transdermal diffusion. It comprises a cylinder body with a cover featuring a groove arranged on the upper surface of the cover body. The cross section of the cover body is concave and a clamping groove is arranged on a side wall of the groove and the cover body and the cylinder body are connected through screw threads or are clamped. The other end of the cylinder body 2 is used for fixing excised skin.

Neither of the identified prior art documents address the same technical problem as the present invention.

SUMMARY OF THE INVENTION

In accordance with a first aspect of the invention there is provided a skin sample culture apparatus which comprises:

a base frame, with a skin sample receiving surface upon which at least part of the skin sample may be placed and which extends across an area defined by the shape of the frame; and a securing member which is releasably connectable to the base frame and a grip which holds the skin sample under tension.

Preferably, the securing member is shaped such that an inner perimeter surface of the securing member is congruent with the shape of the frame.

Preferably, the apparatus further comprises a tensioning cap, mountable on the securing member, the tensioning cap having a tension adjustment mechanism for adjusting the tension across skin sample.

Preferably, the tensioning cap comprises a tensioner which is moveable parallel to the inner perimeter surface of the securing member, such that movement of the tensioner by the tension adjustment means in a direction towards the base will, in use, displace the skin in said direction and increase the tension across the sample of the skin.

Preferably, the tension adjustment means is adjusted by the user.

Preferably the tensioner extends around the inner perimeter of the cap.

Optionally, the tensioner presses against a portion of the upper surface of the skin to move the skin towards the base, thereby increasing the tension across the surface of the skin.

Preferably, the tensioner has a leading surface shaped to move the skin without damaging the skin.

Preferably, the tension adjustment means comprises a plurality of screws which are connected through the cap and securing member, rotation of which adjusts the height of the cap with respect to the securing member.

Optionally, for an annular cap and securing member, the tension adjustment means comprises a first thread on the cap and a second thread on the securing member, rotation of the cap relative to the securing member adjusts the height of the tensioner with respect to the skin sample.

Optionally, the tension adjustment means comprises a cam and follower which converts rotational motion of the cap to linear motion for adjusting the position of the tensioner.

Preferably, the grip comprises a releasable connection between the base frame and the securing member.

More preferably, the grip comprises one or more fixings which connect the base frame to the securing member.

Optionally, the grip comprises a snap fit connection between the base frame and the securing member.

Optionally, the grip comprises a magnetic connection between the base frame and the securing member.

Preferably, the base frame comprises one or more base holes positioned for alignment with one or more corresponding securing frame through hole.

Preferably, the grip comprises a fixing which is sized to connect the one or more securing frames through a hole to an aligned base frame hole.

Preferably, the base frame comprises an annulus.

Preferably, the securing frame comprises an annulus.

Preferably, the base frame comprises a plurality of channels which extend through the side of the receiving frame.

Preferably, at least one of said channels is an upper channel positioned towards a skin mounting surface of the base.

Preferably, at least one of said channels is a lower channel positioned towards the bottom surface of the base frame upon which it rests in use.

Preferably, the channels have a substantially square cross section.

Optionally, the channels have a substantially elliptical cross section.

Preferably, the upper channel is positioned for allowing a gas such as such as air or other ambient gas to exit from the position below a skin sample when it is situated on the base.

Preferably, the height of the upper channel reduces as the channel extends inwards from the outer side of the base frame. Advantageously, this shape encourages such as air or other ambient gas to move out from under a skin sample.

Preferably, the lower channel is positioned for allowing fluid to enter into the space below the skin sample.

Preferably, the lower channel is open at the bottom surface of the base frame.

Preferably, the upper and lower channels are arranged alternately.

Optionally, the upper and lower channels may be arranged in groups.

Optionally, one side of the base may have upper channels and another may have lower channels. This may further assist the removal of gas, such as air or other ambient gas bubbles from the underside of the skin sample when the apparatus is inserted into a culture medium at the side with the lower channels first.

Optionally, the base may have only upper or lower channels.

Preferably, the apparatus comprises a culture medium receptacle.

Preferably the receiving frame and the securing frame are substantially circular.

Optionally, the receiving frame and the securing frame are substantially oval.

Optionally, the receiving frame and the securing frame are substantially square or rectangular.

Preferably, the grip provides a substantially even tensile force across the skin sample.

Preferably, the skin sample culture apparatus further comprises a fluid cap for introducing a fluid into the apparatus.

Preferably, the fluid cap is mounted upon the top of the apparatus to introduce the fluid to the top surface of the sample.

Optionally, the fluid cap is mounted upon the bottom of the apparatus to introduce the fluid to the bottom surface of the sample.

Optionally, the fluid cap is mounted upon both the top and bottom of the apparatus to introduce fluids to the top and bottom surface of the sample.

Preferably, the fluid cap comprises an inlet located at a first position on the fluid cap and an outlet located at a second position on the fluid cap.

Preferably, the inlet is located on the side of the fluid cap.

Optionally, the inlet is located on the top of the fluid cap.

Preferably, the outlet is located on the side of the fluid cap.

Optionally, the outlet is located on the top of the fluid cap.

Preferably, the fluid is a gas.

Optionally, the fluid is a liquid.

In accordance with a second aspect of the invention there is provided a skin sample culture apparatus which comprises:

a base frame, with a skin sample receiving surface upon which at least part of the skin sample may be placed and which extends across an area defined by the shape of the frame;

a securing member which is releasably connectable to the base frame and a grip which holds the skin sample under tension; and a tensioning cap, mountable on the securing member, the tensioning cap having a tension adjustment mechanism for adjusting the tension across the skin sample.

Preferably, the tensioning cap comprises a tensioner which is moveable parallel to the inner perimeter surface of the securing member, such that movement of the tensioner by the tension adjustment means in a direction towards the base will, in use, displace the skin in said direction and increase the tension across the surface of the skin.

Preferably the tensioner extends around the inner perimeter of the cap.

Optionally, the tensioner presses against the upper surface of the skin to move the skin towards the base, thereby increasing the tension across the surface of the skin.

Preferably, the tensioner has a leading surface shaped to move the skin without damaging the skin.

Preferably, the tension adjustment means comprises a plurality of screws which are connected through the cap and securing member, rotation of which adjusts the height of the cap with respect to the securing member.

Optionally, for an annular cap and securing member, the tension adjustment means comprises a first thread on the cap and a second thread on the securing member, rotation of the cap relative to the securing member adjusts the height of the tensioner with respect to the skin sample.

Optionally, the tension adjustment means comprises a cam and follower which converts rotational motion of the cap to linear motion for adjusting the position of the tensioner.

In accordance with a third aspect of the invention there is provided a skin sample culture apparatus which comprises:

a base frame, with a skin sample receiving surface upon which at least part skin sample may be placed and which extends across an area defined by the shape of the frame;

a securing member which is releasably connectable to the base frame and a grip which holds the skin sample under tension; and a fluid cap for introducing a fluid into the apparatus.

Preferably, the fluid cap is mounted upon the top of the apparatus to introduce the fluid to the top surface of the sample.

Optionally, the fluid cap is mounted upon the bottom of the apparatus to introduce the fluid to the bottom surface of the sample.

Optionally, the fluid cap is mounted upon both the top and bottom of the apparatus to introduce fluids to the top and bottom surface of the sample.

Preferably, the fluid cap comprises an inlet located at a first position on the fluid cap and an outlet located at a second position on the fluid cap.

Preferably, the inlet is located on the side of the fluid cap.
Optionally, the inlet is located on the top of the fluid cap.
Preferably, the outlet is located on the side of the fluid cap.
Optionally, the outlet is located on the top of the fluid cap.
Preferably, the fluid is a gas.
Optionally, the fluid is a liquid.

In accordance with a fourth aspect of the invention there is provided an apparatus for measuring the tension in a skin sample culture apparatus in accordance with the first aspect of the invention, the apparatus comprising:

a spacer which couples the force meter to the skin sample culture apparatus;

a probe which is extendable from the spacer for contact with a skin sample and which applies a force to the skin sample;

a force meter for measuring the force applied wherein the amount of force for a given displacement, defined by the spacer length, provides a measure of skin tension.

Preferably, the probe applies a measurable force to the surface of a skin sample which is held in the skin sample holder.

Preferably, the force is applied by contacting the probe with the surface of the skin sample displacing the skin a predetermined amount so as to stretch the skin, wherein the amount of force for a given displacement provides a measure of skin tension.

Preferably, where an annular skin sample holder is used, a correction factor is applied to the force measurement to account for the effect of the radius of the skin sample holder.

Preferably, the probe further comprises computing means for calculating the correction factor.

For example, the computing mean may be contained in the probe as hardware, firmware and/or software or may be a separate module or device.

Preferably, the probe is spherical.
Optionally, the probe is conical.
Optionally, the probe is cylindrical.

BRIEF DESCRIPTION OF THE DRAWINGS

The present invention will now be described with reference to the accompanying drawings in which:

FIG. 3A is a perspective view of a third embodiment of a base in accordance with the present invention, FIG. 3B is a perspective view of a section of the base of FIG. 3A and FIG. 3C is a side view of the base of FIG. 3A in cross section;

FIG. 6A to FIG. 6L shows a second example of a process for attaching a skin sample to an apparatus in accordance with the present invention;

FIG. 7A to FIG. 7H shows an example of a process for depositing an apparatus in accordance with the present invention in a culture dish containing medium;

DETAILED DESCRIPTION OF THE DRAWINGS

The present invention provides a novel means by which cultured skin samples may be kept under tension. Maintaining the skin samples under tension is beneficial because it extends the viable lifetime and the quality of the skin. In addition, the present invention allows the skin to be quickly mounted with minimal waste, cultured in a standard $CO_2$ incubator, without the need to suture the skin sample in place. Suturing is very time consuming both when the sample is being stored in a sample dish and when the sample is subsequently to be removed from the dish.

Figure 1:
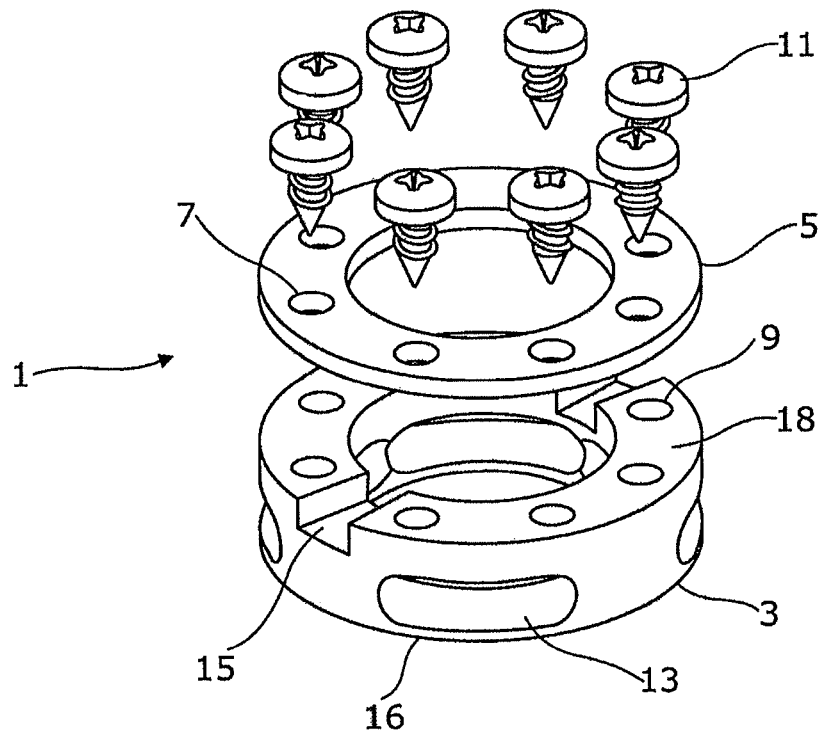
FIG. 1 shows an exploded perspective view of a first embodiment of a skin sample culture apparatus in accordance with the present invention.

FIG. 1 shows a first embodiment of a skin sample storage apparatus in accordance with the present invention.

FIG. 1 shows the apparatus 1 which has a base 3 upon which a skin sample is placed in use, and a cap 5 which is placed on top of a skin sample, in use. Through holes 7 in the cap 5, are aligned with holes 9 in the base 3 and screws 11 or other suitable fixings are used to attach the cap 5 to the base 3.

In this example of the present invention, the screws provide for the removable attachment of the cap 5 to the base 3. The base further comprises lower channels 13 and two upper channels 15 which extend radially through the circumference of the base 3. The lower channels 13 are positioned towards the bottom surface 16 of the base 3, and the upper channels are placed at the top surface 18 of the base 3. In this example of the invention, the lower channel 13 is a closed channel at the bottom of the base 3. The upper channel 15 is open at its top.

Figure 2:
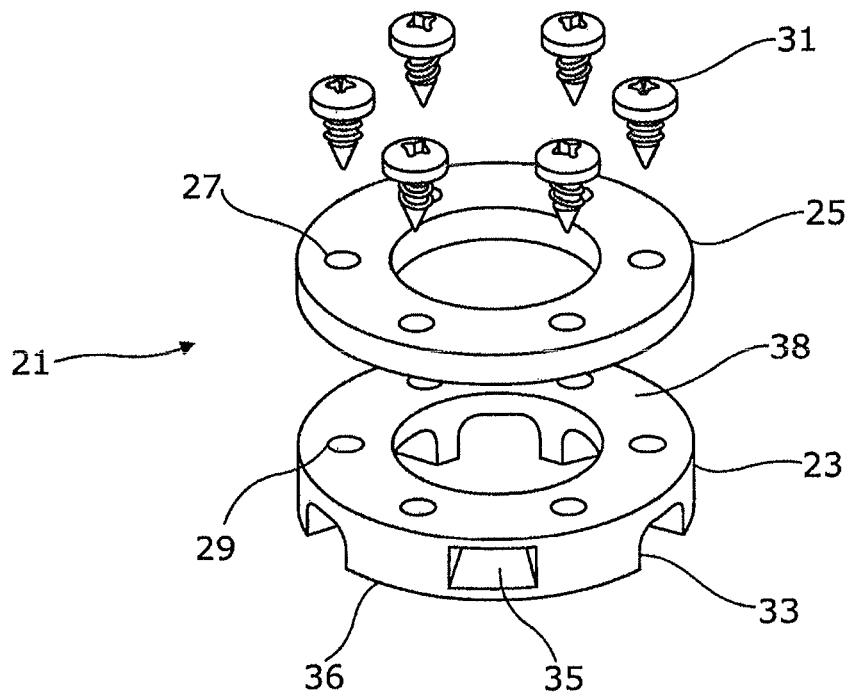
FIG. 2 an exploded view of a second embodiment of a skin sample culture apparatus in accordance with the present invention.

FIG. 2 shows a second embodiment of skin sample culture apparatus base in accordance with the present invention.

FIG. 2 shows the apparatus 21 which has a base 23 upon which a skin sample is placed in use, and a cap 25 which is placed on top of a skin sample, in use. Through holes 27 in the cap 25, are aligned with holes 29 in the base 23 and screws 31 or other suitable fixings are used to attach the cap 25 to the base 23.

In this example of the present invention, the screws provide for the removable attachment of the cap 25 to the base 23. The base further comprises lower channels 33 and upper channel 35 which extend radially through the circumference of the base 23. The open lower channels 33 are positioned towards the bottom surface 36 of the base 23, and the enclosed upper channel is placed towards the top surface 38 of the base 23.

In this example of the invention, the upper channel 35 is closed at the top surface of the base 23. The lower channels 33 are open at the bottom surface.

FIGS. 3A, 3B and 3C show the base 43 of a third embodiment of a skin sample culture apparatus base in accordance with the present invention.

The base 43 comprises base holes 45, lower channels 47 and upper channel 49 which extend radially through the circumference of the base 43. In this embodiment, the lower channels are open at the bottom surface 54 of the base 43.

The upper channel 49 is enclosed. As shown in FIG. 3C, the top surface 51 of the upper channel 49 is at an angle with respect to the bottom of the base 54 such that the end of the channel 49 at the outermost part of the base 43 is higher than the end of the channel at the innermost part of the base 43. The angle 53 illustrated in this embodiment of the invention is approximately 4°.

The angle of inclination of the top surface assists with the passage of trapped air from under a skin sample when the apparatus is in use.

In this and other examples of the present invention, a single upper channel and multiple lower channels are arranged at an equal spacing around the base 43. In other examples, multiple upper or lower channels may be present or multiple upper and lower channels may be arranged alternately or in groups; for example, one side of the base may have upper channels and another may have lower channels. This may further assist the removal of air bubbles from the underside of the skin sample.

FIG. 4 shows an example of a method by which the skin sample 65 is attached to a skin sample culture apparatus in accordance with the present invention. FIG. 4A shows a mounting mat 61 upon which is placed a skin sample 65.

Figure 4C:
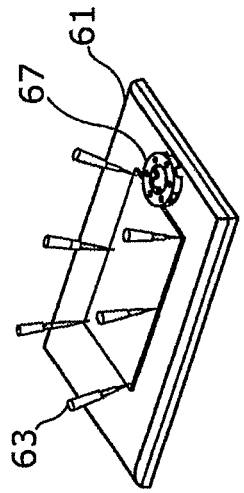
FIG. 4A to FIG. 4F show an example of a process for attaching a skin sample to an apparatus in accordance with the present invention.
Figure 4F:
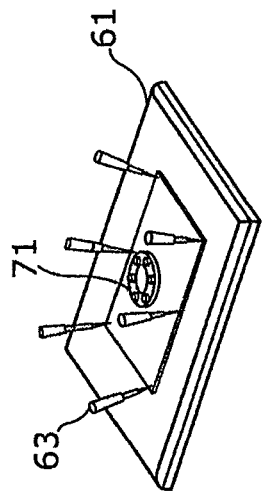
Figure 4B:
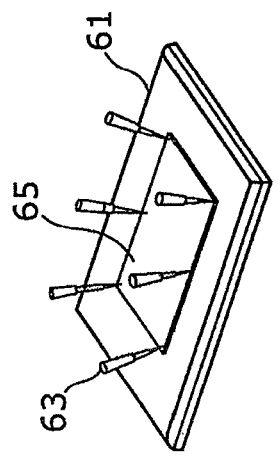

FIG. 4B shows the mounting mat 61 and the skin sample 65 which has been stretched across the mounting mat 61 and secured in position by pins 63 which are pushed through the skin sample 65 into the mounting mat 61.

FIG. 4C shows a base 67 in accordance with the present invention positioned upon the mounting mat 61.

Figure 4E:
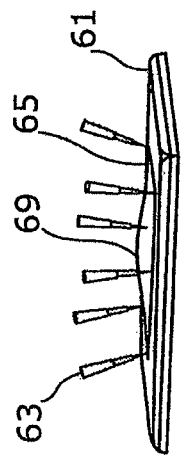
Figure 4A:
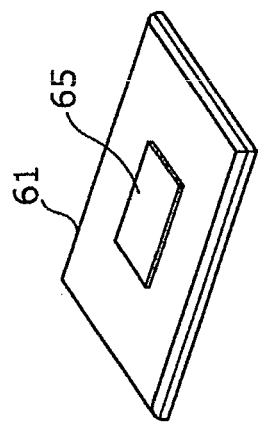
Figure 4D:
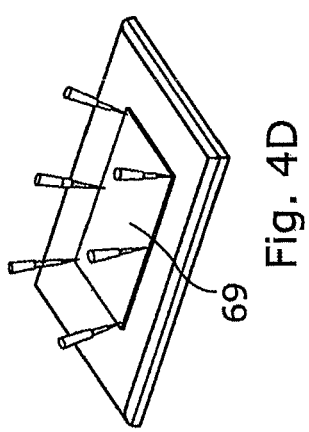

FIG. 4D shows that the base 67 has been moved from its position in FIG. 4C and has been moved under the stretched skin sample to position 69. FIG. 4E is a side perspective view at the base 67 in position 69 between the skin sample 65 and the mat 61.

FIG. 4F shows a cap 71 in accordance with the present invention, placed on top of the skin 65 aligned with the base 67 at position 69.

Figure 5:
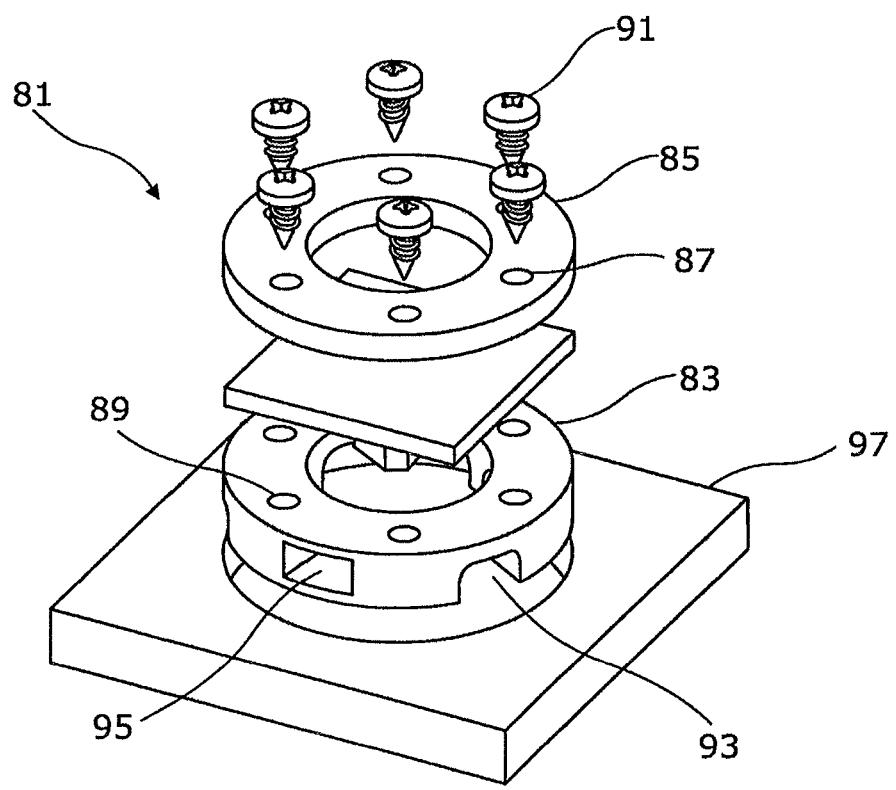
FIG. 5 is an exploded perspective view of the third embodiment of the present invention.

FIG. 5 shows another example of a skin sample culture apparatus in accordance with the present invention.

FIG. 5 shows an embodiment of a skin sample storage apparatus in accordance with the present invention.

FIG. 5 shows the apparatus 81 which has a base 83 upon which a skin sample is placed in use, and a cap 85 which is placed on top of a skin sample, in use. Through holes 87 in the cap 85, are aligned with holes 89 in the base 83 and screws 91 or other suitable fixings are used to attach the cap 85 to the base 83. It is mounted on mat 97.

In this example of the present invention, the screws 91 provide for the removable attachment of the cap 85 to the base 83. The base is similar to that described with reference to FIGS. 3A to 3C. The base 83 comprises base holes 89, lower channels 93 and upper channels 95 which extend radially through the circumference of the base 83.

The upper channels 95 are enclosed and as with the example of FIGS. 3A to 3C, the top surface of the upper channel is at an angle with respect to the bottom of the base such that the end of the channel 95 at the outermost part of the base 83 is higher than the end of the channel at the innermost part of the base 83. The angle of inclination of the top surface assists with the passage of trapped air from under a skin sample when the apparatus is in use.

In this and other examples of the present invention, a single upper channel and multiple lower channels are arranged at an equal spacing around the base 43. In other examples, multiple upper and lower channels may be arranged alternately or in groups; for example, one side of the base may have upper channels and another may have lower channels. This may further assist the removal of air bubbles from the underside of the skin sample.

FIGS. 6A-L and 7A-H show a method by which an example of a skin sample culture apparatus in accordance with the present invention is used.

FIG. 6A shows a mounting mat 97, a skin sample 103 and a base 83. The base 83 is placed in a mounting mat inset 99. The mat 97 has sufficient thickness such that the depth of the inset ensures that the top surface of the base 83 is flush with the top surface of the mounting mat 97.

FIGS. 6B to 6F show the process by which a skin sample is placed upon a mounting mat which has a base 83 positioned in the inset 99. The skin 103 is fixed to the mounting mat on one side with pins 101. FIG. 6C shows the skin 103 being stretched across the top of the base 83 and secured to the mounting mat 97 with a third pin 101. FIG. 6D shows a fourth corner of the skin being stretched across the top of the base 83 and secured to the mounting mat 97 with a fourth pin 101.

FIG. 6E shows additional pins 101 which attach the skin sample 103 to allow even tension throughout the skin.

FIG. 6F shows a biopsy punch 105 which is used to cut holes in the skin to allow the attachment of screws to the base 83 through the cap 85 which has been positioned on top of the skin sample 103 in alignment with the base 83. The screws are placed in the cap holes 87 and are driven through the cut holes in the skin 103 and held in the base holes which are aligned with the cap holes 87. As shown in FIGS. 6G to 6J, this process allows for the removal of the pins 101 and retains the skin sample 103 under tension clamped between the cap 83 and the base 85. FIG. 6K shows the skin sample culture apparatus being removed from the mat 97. FIG. 6L shows excess skin from the edges of the sample trimmed off.

FIGS. 7A-7D show the culture dish 111 containing a culture medium 113 and a skin sample culture apparatus 115 being lowered towards the culture dish 111.

FIGS. 7B-7D show the skin sample culture apparatus 115 being lowered at an angle towards the culture dish. Advantageously it has been found that, lowering the skin sample culture apparatus 115 at an angle with the air channel angled upwards encourages any air which might be between the skin sample and the culture medium towards the higher side of the skin sample culture apparatus and therefore reduces the risk that the air will be trapped under the skin sample. Trapped air prevents the culture medium from having full contact with the skin sample and therefore, may cause the skin sample to degrade.

During the process of lowering the sample and once it is in position as shown in FIG. 7F, a base which has angled upper channels as shown in the example of FIGS. 3A-3C will further assist with the removal of trapped air by providing an easy path for the trapped air's exit from beneath the skin sample. Once the skin sample culture apparatus is in position, a cover 123 is placed upon the culture dish 111.

The above embodiments show the grip element comprising a number of screws which connect the base to the cap. Other grips may be used, such as a snap fit connection or a magnet, for example.

Figure 8:
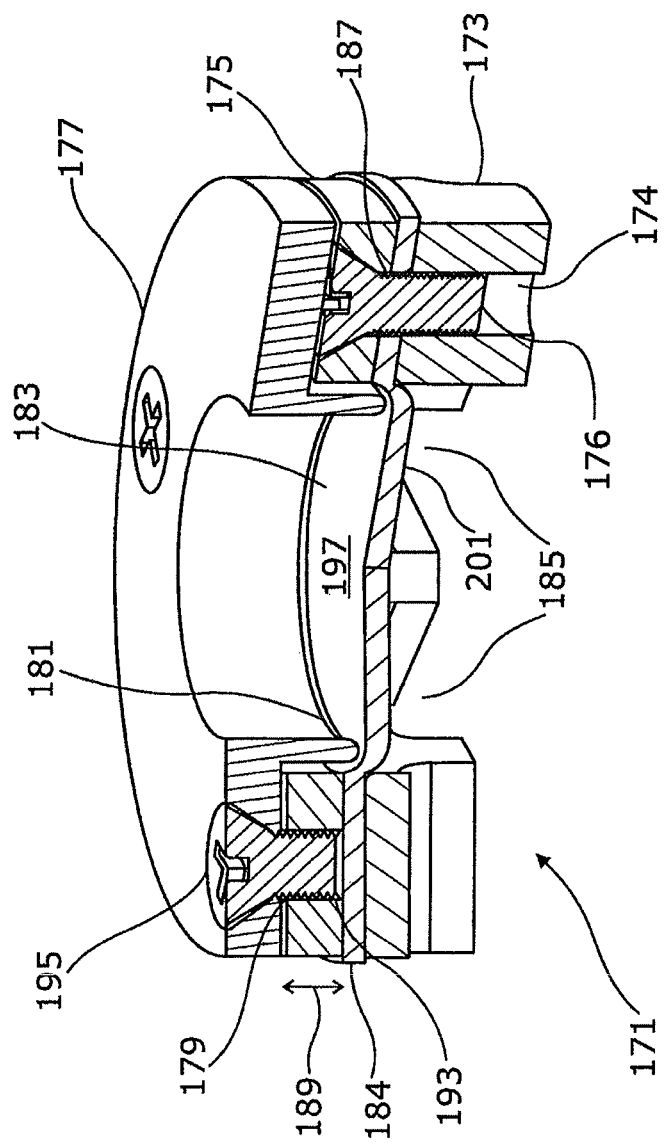
FIG. 8 is a perspective cut-away view of another embodiment of the present invention.

FIG. 8 is a perspective cut-away view of another embodiment of the present invention.

FIG. 8 shows the apparatus 171 with a base 173, a securing member 175 and a tensioner cap 177. The base 173 has base holes 174 which receive fixings 176. The base is annular in shape and further comprises channels 185 which extend through the perimeter of the base allowing culture medium, air and other fluids to move through the space at or below the underside 201 of the skin sample 183.

The securing member 175 is annular in shape and congruent with the base 173. Securing member holes 187 extend through the securing member 175 and, in use, are aligned with the base holes 174. The skin sample 183 is secured in position upon the apparatus by placing the skin sample 183 between the base 173 and securing member 175 to or slightly beyond the outer circumference of the securing member 175 and base 173. A screw is inserted through the securing member hole 187 and the base hole 174 and the screw is tightened to secure the skin sample in position between the base 173 and securing member 175.

The tensioning adjustment mechanism is a cap 177 is annular in shape and is positioned on top of the securing member 175 and is congruent with the securing member 175 except that a tensioner 181 extends downwards from the inner circumference of the tensioning cap, slightly beyond the inner surface of the securing member 175. The tensioner is sized such that it extends beyond the 'bottom surface' of the tensioner cap 177 to be longer than the securing cap depth 189.

A securing member/tensioner cap hole 193 is threaded. The tensioner cap 177 has a tension adjustment mechanism 179 comprising screw 195 which extends through the tensioner cap 177 into the securing member/tensioner cap hole 193.

In use, a skin sample 183 is firstly secured in position between the base 173 and the securing member 175. The tensioner cap 177 is fitted on the top of securing member 175. In order to increase the tension across the surface of the skin the tension cap screws 195 are turned. This moves the tensioner cap 177 closer to the securing member 175. In this embodiment of the present invention, the tensioner 181 is rigidly fixed to the tension adjustment mechanism 179 of the tensioner cap 177. Tightening the tensioner cap screw 195 moves the tensioner 181 vertically towards the upper surface 197 of the skin sample 183. Upon contact with the skin sample surface 197, further tightening of the tension cap screw 195 will push the tensioner 181 and the edges of the skin 183 downwards, pulling the skin tight across its surface and increasing the tension across the sample.

Figure 9:
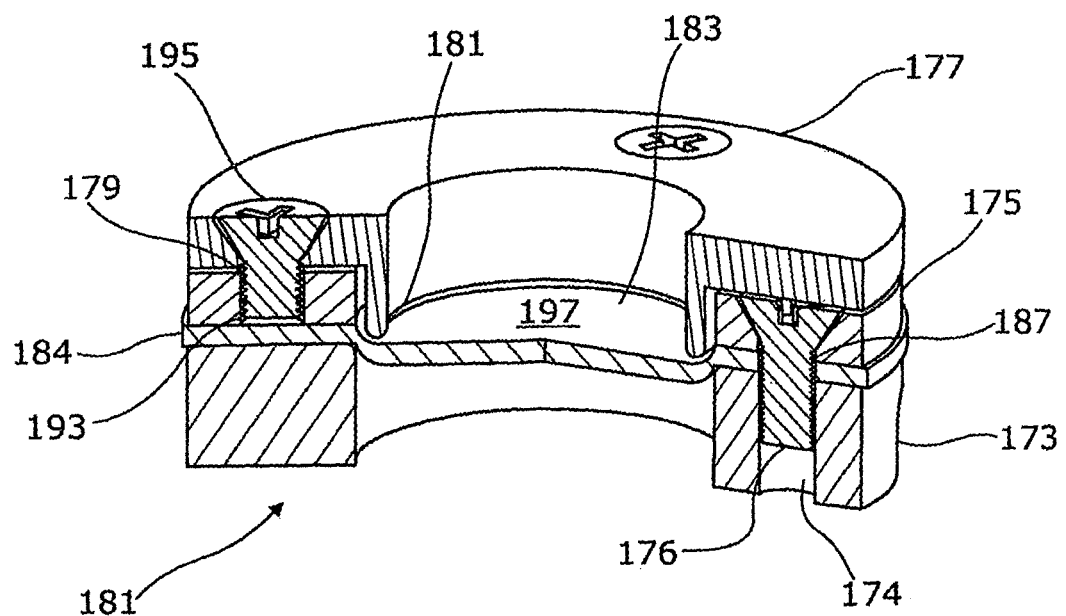
FIG. 9 is a perspective cut-away view of a modified version of the embodiment of the present invention shown in FIG. 8.

FIG. 9 is a perspective cut-away view of a modified version 181 of the embodiment of the present invention shown in FIG. 8 on which the channels 185 of FIG. 8 have been removed. The embodiments of FIGS. 8 and 9 provide a quick and easy way of adjusting the tension in the skin sample.

Figure 10:
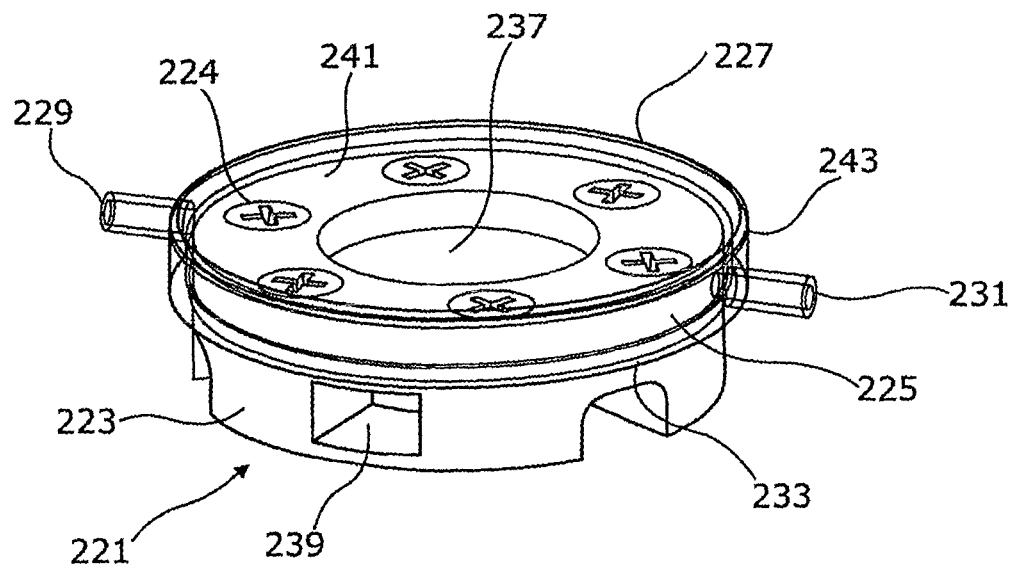
FIG. 10 is a perspective view of another embodiment of the present invention.

FIG. 10 is a perspective view of another embodiment of the present invention. FIG. 10 shows the apparatus 221 with a base 223, a securing member 225 and a fluid cap 227. The base has holes (not shown) which receive fixings 224. The base is annular in shape and further comprises channels 239 which extend through the perimeter of the base, allowing the culture medium, air and other fluids to move through the space at or below the underside of the skin sample 237.

The fluid cap 227 is substantially cylindrical in shape having an enclosed top surface 241, an enclosed side surface 243 with a seal 233 on its lower circumference, at the open bottom surface of the cylindrical sloped cap. The seal is designed to retain the fluid in the space at or around the top surface of the skin sample 237. The inlet 229 is connectable to a fluid source and the outlet 231 is connected to a fluid collector. In use, the fluid cap 227 is placed over the securing member and pushed downwards into place and the seal 233 holds the fluid cap in position. A fluid source is connected to the fluid cap inlet. The fluid may be introduced as a batch into the fluid cap, in which the outlet 231 is closed and once the required amount of fluid has been added, the inlet is closed. Alternatively, the fluid may be introduced continuously so a continuous flow of fluid passes through the fluid cap 227, in this case the inlet 229 and the outlet 231 remain open, the outlet being connected to a fluid collection vessel.

The fluid cap will allow the ability to culture skin such that the atmosphere (e.g., humidity, gas composition, etc.) at the surface of the skin can be controlled separately from the atmosphere of the incubator.

In another embodiment of the present invention, the apparatus incorporates a tensioning cap and a fluid cap thereby allowing the user to alter the skin sample tension and perform experiments which change the medium to which the top layer of the skin sample is exposed. In another embodiment of the present invention, the apparatus incorporates a fluid cap on both the top and bottom sides of the device allowing experiments which change the medium to which both the upper and lower sides of the skin sample are exposed to.

Figure 11:
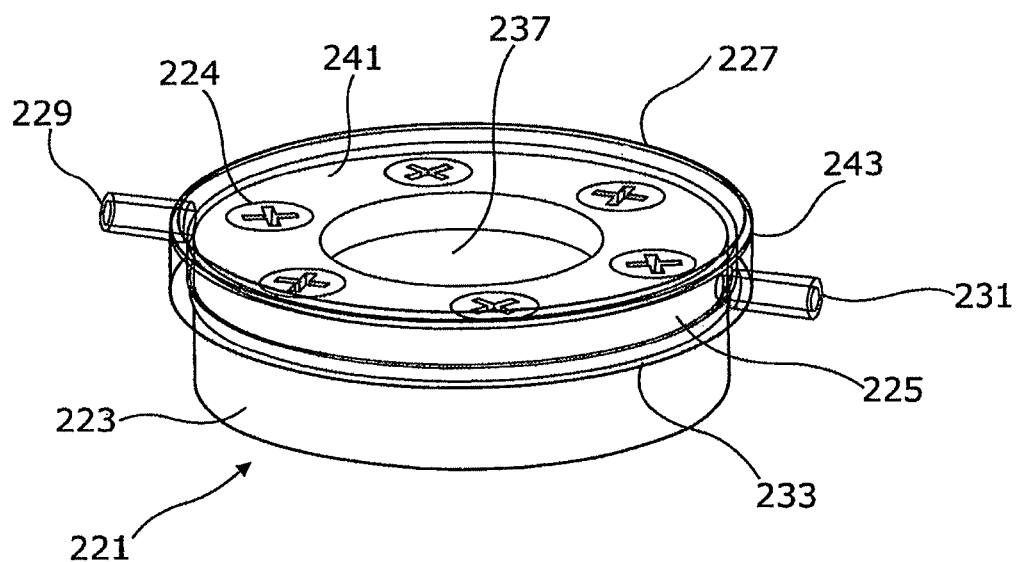
FIG. 11 is a perspective view of a modified version of the embodiment of the present invention shown in FIG. 10.

FIG. 11 is a perspective view of a modified version of the embodiment of the present invention 251 shown in FIG. 10 with the base channels absent.

Figure 12:
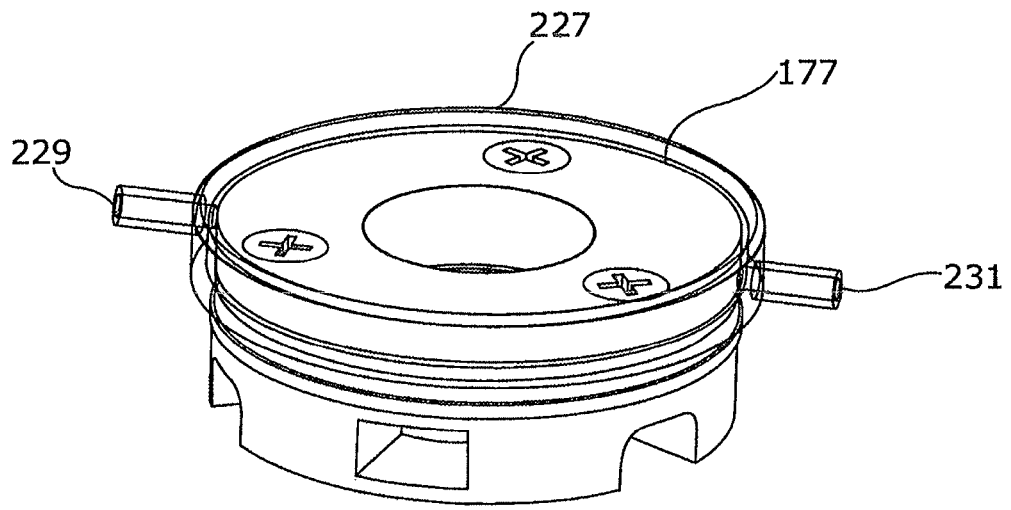
FIG. 12 is a perspective view of an embodiment of the present invention which incorporates the features of FIGS. 8 and 10.

FIG. 12 is a perspective view of an embodiment of the present invention which incorporates features of FIGS. 8 and 10. It shows the tensioning cap 177 and base of FIG. 8 and the fluid cap 227 of FIG. 10 with a base similar to that shown in FIGS. 8 and 10.

In another embodiment of the present invention the tensioner is resiliently mounted and attached to a force meter such that the force applied by the tension adjustment mechanism is measurable.

Figure 13:
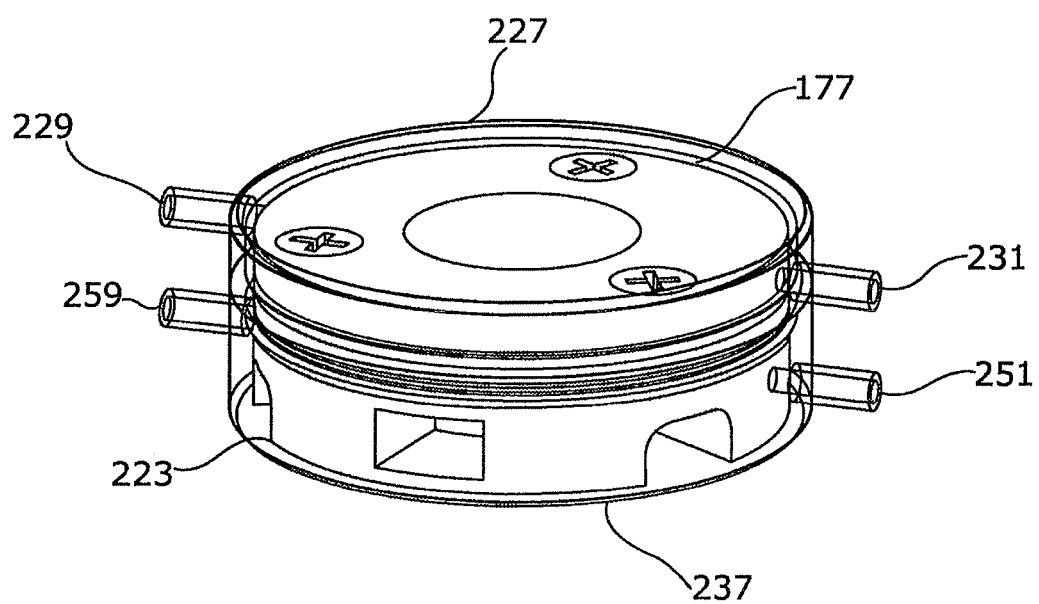
FIG. 13 is a perspective view of a modified version of the embodiment of the present invention shown in FIG. 12.

FIG. 13 is a perspective view of an embodiment of the present invention shown in FIG. 12 with the addition of a fluid cap to the bottom of the apparatus. It shows the tensioning cap 177 and a base 223 with a top fluid cap 227 and bottom fluid cap 237. The bottom fluid cap 237 features a fluid inlet 259 and fluid outlet 251 which allow control of the atmosphere at the bottom surface of the skin sample.

Figure 14:
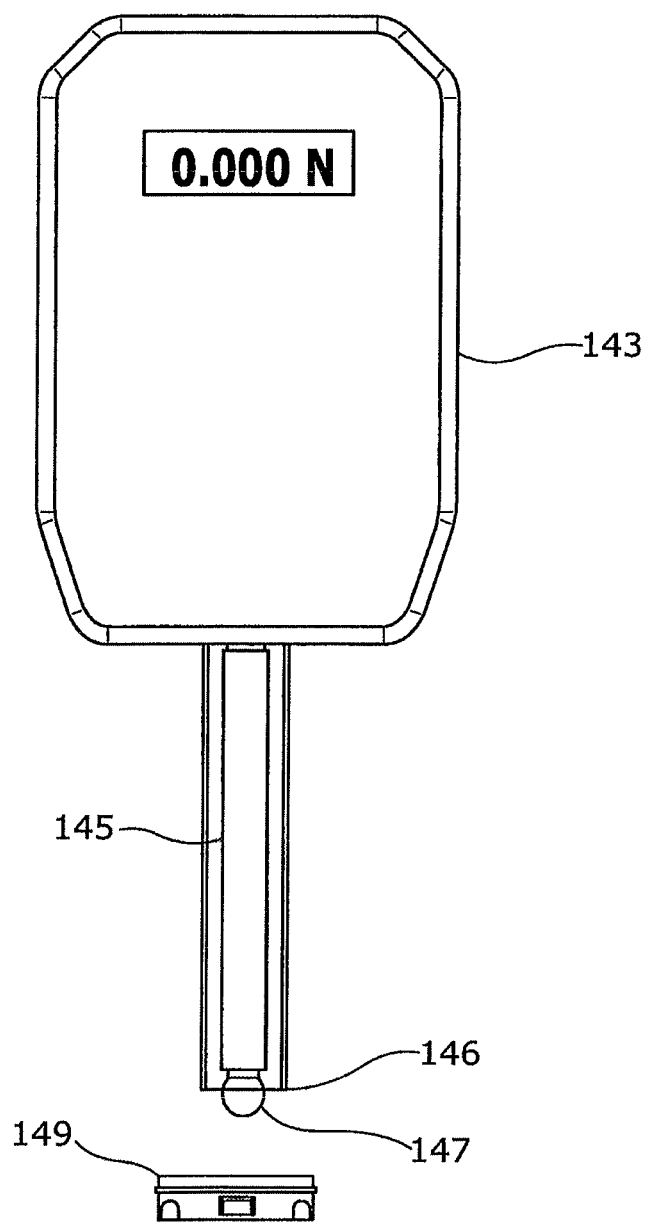
FIG. 14 is a side view of a force meter in accordance with the present invention.

FIG. 14 shows an apparatus for measuring the tension in a skin sample which has been placed in a skin sample culture apparatus in accordance with the present invention.

The apparatus comprises a force meter 143, a spacing collar 146 which slides over the probe shaft 145 and extends downwards from the body of the force meter 143. The collar 146 is a cylindrical tube with a diameter and circumferences which matches that of the cap such that the end of the collar 146 rests upon the cap of a skin sample culture apparatus 149. The spherical indenter exerts a force upon the skin sample.

Figure 15A:
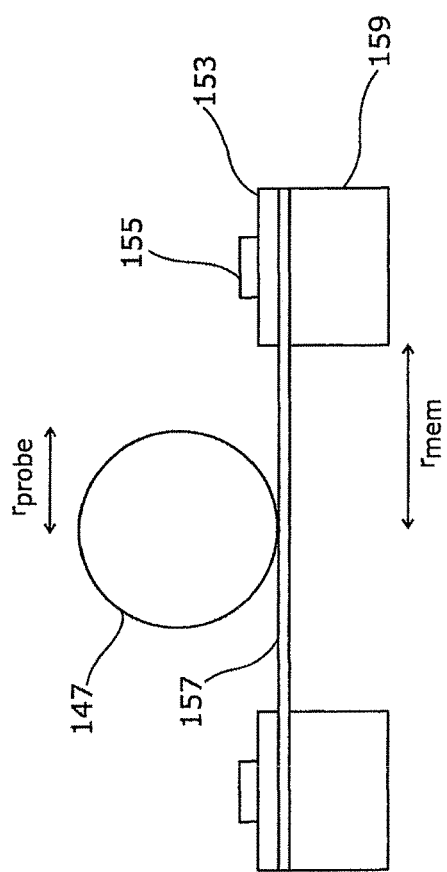
FIGS. 15A and 15B are schematic diagrams showing the operation of the force meter.
Figure 15B:
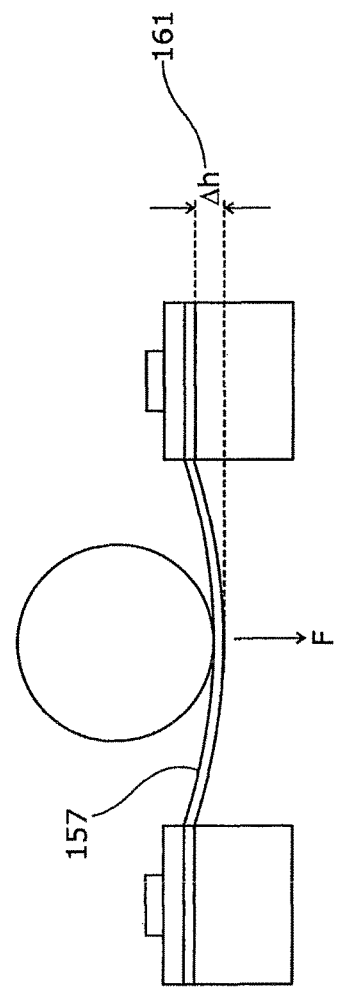

FIGS. 15A and 15B are schematic diagrams which illustrate the operation of the apparatus 143.

FIG. 15A shows the spherical indenter 147 resting upon the skin sample 157 at the centre of the sample. The cap 153, fixings 155 and base 159 are also shown in the diagram. When a known displacement Δh 161, defined by the collar 146 length, is exerted upon the skin sample 157, a force reading is recorded. This provides a measure of skin tension.

Where the radii are different, it is necessary to account for the effect of the radius on the measured value of tension.

The elastic modulus E of the membrane mounted in the culture device, defined as the relationship between stress (force per unit area) and strain (proportional deformation), will be used to relate tension measurements in devices of different diameters using variable indentation distances.

When the membrane is mounted in the culture device at the correct tension it will possess a certain elastic modulus.

It is assumed the probe is in frictionless contact and for simplicity that the deformed membrane conforms to a conical geometry with a uniform strain. It is also assumed the membrane is a linearly elastic material.

The probe applies an average stress over the membrane given by, $$\sigma = \frac{F}{A_{CS}}$$

Where F is the normal force applied by the probe and $A_{CS}$ is the cross sectional area of the membrane.

Due to this stress, the membrane deforms to a ~conical geometry with a surface area defined as, $$A_{cone} = \pi r \sqrt{r^2 + h^2}$$

Where r is the membrane diameter and h is the indentation distance, or equally the height of the cone formed by the stretched membrane. The area strain ε over the stretched membrane is given by, $$\varepsilon = \frac{\Delta A}{A_0}$$

Where ΔA, the change in area of the membrane, is given by, $$\Delta A = A_{cone} - A_0$$

$$\Delta A = \pi r \sqrt{r^2 + h^2} \pi r^2$$

Therefore ε can be written as, $$\varepsilon = \frac{\sqrt{r^2 + h^2} - r}{r}$$

The elastic modulus E can now be fully defined as, $$E = \frac{\sigma}{\varepsilon}$$

In examples of the present invention described herein the skin sample holder our has a 15 mm diameter culture device with a 3 mm indentation/push depth (15-3) to characterise the optimum tension $F_0$ required in our membrane.

Therefore this will be our reference from which the conversion factors will be calculated, however, this approach can be applied generally to any diameter/depth values used for membrane characterisation.

To find the required probe force reading $F_x$ on a different diameter device we equate the elastic moduli.

$$E_0 = E_x$$

$$\frac{\sigma_0}{\varepsilon_0} = \frac{\sigma_x}{\varepsilon_x}$$

$$\frac{F_0/A_{CS_0}}{\varepsilon_0} = \frac{F_x/A_{CS_x}}{\varepsilon_x}$$

$$F_0 = \frac{F_x A_{CS_0} \varepsilon_0}{A_{CS_x} \varepsilon_x}$$

Using the values for our membrane characterisation (15-3) we can generate a matrix of conversion/correction factors to allow testing of devices of different diameters and also using different indentation depths/distances.

The correction factor (λ) relates the measured force as follows, $$F_{15-3} = \lambda F_{x-y}$$

Here, we see that, as expected, the correction factor for a 15 mm diameter device with an indentation depth of 3 mm is unity or 1.

Maintaining the device diameter at 15 mm but increasing indentation depth we see the factor decrease which is logical considering the membrane is stretched to a greater extent with an increase indentation. Similarly, with a smaller diameter device/membrane the correction factor decreases for a given indentation depth.

Due to the assumption of a linearly elastic material it is advised that strain is below 10% during tension measurements, i.e. the membrane is not stretched by an amount greater than 10% by the probe.

It will be appreciated that it is convenient for the apparatus and its component parts to have a generally circular form. Other shapes may be used, such as square, oval or rectangular, and as such fall within the scope of the present invention.

Improvements and modifications may be incorporated herein without deviating from the scope of the invention.

The invention claimed is:

1. A skin sample culture apparatus which comprises:
 a base frame, with a skin sample receiving surface upon which a part of the skin sample may be placed and which extends across an open area defined by a shape of the frame; and
 a securing member and a grip which are releasably connectable to the base frame which holds the skin sample under tension;
 wherein the base frame comprises a plurality of channels which extend through the side thereof and wherein, at least one of said channels is an upper channel positioned towards the skin sample receiving surface of the base frame, at least one of said channels is a lower channel positioned towards the bottom surface of the base frame upon which it rests in use in a culture medium receptacle containing culture medium;
 wherein, the upper channel is positioned for allowing air or other ambient gas to exit from the position below a skin sample when it is situated on the base frame within culture medium receptacle containing culture medium, and
 wherein, the apparatus further comprises a tensioning cap, mountable on the securing member, the tensioning cap having a tension adjustment mechanism for adjusting the tension across the skin sample.

2. An apparatus as claimed in claim 1 wherein, the tensioning cap comprises a tensioner which is moveable parallel to the inner perimeter surface of the securing member, such that movement of the tensioner by the tension adjustment mechanism in a direction towards the base will, in use, displace the skin in said direction and increase the tension across the skin sample.

3. An apparatus as claimed in claim 2 wherein, the tensioner extends around the inner perimeter of the tensioning cap.

4. An apparatus as claimed in claim 2 wherein, the tensioner presses against a portion of the upper surface of the skin to move the skin towards the base, thereby increasing the tension across the skin sample.

5. An apparatus as claimed in claim 2 wherein, the tensioner has a leading surface shaped to move the skin without damaging the skin.

6. An apparatus as claimed in claim 1 wherein, the tension adjustment mechanism comprises a plurality of screws which are connected through the tensioning cap and securing member, rotation of which adjusts the height of the tensioning cap with respect to the securing member.

7. An apparatus as claimed in claim 1 wherein, the grip comprises a releasable connection between the base frame and the securing member.

8. An apparatus as claimed in claim 1 wherein, the grip comprises one or more fixings which connect the base frame to the securing member, or a snap fit connection between the base frame and the securing member, or a magnetic connection between the base frame and the securing member.

9. An apparatus as claimed in claim 1 wherein, the upper channel height reduces as the channel extends inwards from the outer side of the base frame which encourages air or other ambient gas to move out from under a skin sample.

10. An apparatus as claimed in claim 1 wherein, at least one of said channels is a lower channel positioned towards the bottom surface of the base frame upon which it rests in use and wherein the lower channel is positioned for allowing fluid to enter into the space below the skin sample.

11. An apparatus as claimed in claim 1 wherein, one side of the base frame has upper channels and another has lower channels to further assist the removal of gas bubbles from the underside of the skin sample when the apparatus is inserted into the culture medium at the side with the lower channels first.

12. A skin sample culture apparatus as claimed in claim 1 wherein, the skin sample culture apparatus further comprises a fluid cap for introducing a fluid into the apparatus.

13. A skin sample culture apparatus as claimed in claim 12 wherein, the fluid cap comprises an inlet located at a first position on the fluid cap and an outlet located at a second position on the fluid cap.

* * * * *